US011311220B1

United States Patent
Al-Saggaf et al.

(10) Patent No.: US 11,311,220 B1
(45) Date of Patent: Apr. 26, 2022

(54) DEEP LEARNING MODEL-BASED IDENTIFICATION OF STRESS RESILIENCE USING ELECTROENCEPHALOGRAPH (EEG)

(71) Applicant: King Abdulaziz University, Jeddah (SA)

(72) Inventors: Ubaid M. Al-Saggaf, Jeddah (SA); Syed Saad Azhar Ali, Kampar (MY); Muhammad Moinuddin, Jeddah (SA); Rumaisa Abu Hasan, Seri Iskandar (MY); Mohammed U. Alsaggaf, Jeddah (SA)

(73) Assignee: King Abdulaziz University, Jeddah (SA)

( * ) Notice: Subject to any disclaimer, the term of this patent is extended or adjusted under 35 U.S.C. 154(b) by 0 days.

(21) Appl. No.: 17/498,379

(22) Filed: Oct. 11, 2021

(51) Int. Cl.
*A61B 5/16* (2006.01)
*A61B 5/374* (2021.01)
(Continued)

(52) U.S. Cl.
CPC .............. *A61B 5/165* (2013.01); *A61B 5/291* (2021.01); *A61B 5/374* (2021.01); *A61B 5/378* (2021.01);
(Continued)

(58) Field of Classification Search
CPC ......... A61B 5/165; A61B 5/291; A61B 5/374; A61B 5/378; A61B 5/38; A61B 5/384; A61B 5/4884; A61B 5/7264
(Continued)

(56) References Cited

U.S. PATENT DOCUMENTS 8,529,447 B2 * 9/2013 Jain ...................... A61B 5/0024
600/300
8,540,629 B2 * 9/2013 Jain ...................... A61B 5/165
600/300
(Continued)

FOREIGN PATENT DOCUMENTS

WO    WO 2020/121299 A1    6/2020

OTHER PUBLICATIONS

Albert Rizzo, et al., "STRIVE: Stress Resilience In Virtual Environments: A Pre-Deployment VR System for Training Emotional Coping Skills and Assessing Chronic and Acute Stress Responses", Medicine Meets Virtual Reality, IOS Press, vol. 19, 2012, pp. 379-385.

(Continued)

*Primary Examiner* — Navin Natnithithadha
(74) *Attorney, Agent, or Firm* — Oblon, McClelland, Maier & Neustadt, L.L.P.

(57) ABSTRACT

A device, method, and non-transitory computer readable medium for identification of stress resilience. The method for identification of stress resilience includes stimulating a human subject by at least one of a plurality of stressful events in a virtual reality environment, acquiring multichannel real-time electroencephalograph (EEG) signals by an EEG monitor worn by a human subject, recording the real-time EEG signals received during the stressful event, transmitting the real-time EEG signals to a computing device. The computing device generates a plurality of filtered brain wave frequencies related to the stressful event by filtering the multichannel real-time EEG signals, classifies the brain wave frequencies by frequency level by applying the filtered brain wave frequencies to the deep learning model, applies each frequency level associated with the stressful event to the convolutional neural network, and (Continued)

identifies a level of stress resilience of the human subject associated with the stressful event.

20 Claims, 11 Drawing Sheets

(51) Int. Cl.
    *A61B 5/38*     (2021.01)
    *A61B 5/384*    (2021.01)
    *A61B 5/378*    (2021.01)
    *A61B 5/291*    (2021.01)
    *A61B 5/00*     (2006.01)

(52) U.S. Cl.
    CPC ............... *A61B 5/38* (2021.01); *A61B 5/384* (2021.01); *A61B 5/4884* (2013.01); *A61B 5/7264* (2013.01)

(58) Field of Classification Search
    USPC .................................................. 600/544–545
    See application file for complete search history.

(56) References Cited

U.S. PATENT DOCUMENTS

| | | | | |
|---|---|---|---|---|
| 10,136,856 B2* | 11/2018 | Tzvieli | ................ | A61B 5/7267 |
| 10,231,673 B2* | 3/2019 | Jain | .................... | A61B 5/0006 |
| 10,390,764 B2* | 8/2019 | Jain | ................... | A61B 5/02416 |
| 10,456,088 B2* | 10/2019 | Jain | ........................ | G16H 40/67 |
| 10,478,131 B2* | 11/2019 | Jain | ...................... | A61B 5/7203 |
| 10,812,424 B1* | 10/2020 | Bommaraju | .......... | H04L 51/046 |
| 11,051,748 B2* | 7/2021 | Keane | .................. | A61B 5/7267 |
| 11,179,089 B1* | 11/2021 | Al-Saggaf | ............. | A61B 5/374 |
| 2010/0145215 A1* | 6/2010 | Pradeep | ............... | A61B 5/4035 |
| | | | | 600/546 |
| 2014/0316230 A1* | 10/2014 | Denison | ................. | A61B 5/168 |
| | | | | 600/545 |
| 2017/0071523 A1* | 3/2017 | Jain | ........................ | A61B 5/746 |
| 2017/0071537 A1* | 3/2017 | Jain | ...................... | A61B 5/0013 |
| 2017/0071546 A1* | 3/2017 | Jain | ........................ | G16H 40/63 |
| 2017/0071551 A1* | 3/2017 | Jain | ...................... | A61B 5/7282 |
| 2017/0367651 A1* | 12/2017 | Tzvieli | ................ | A61B 5/0075 |
| 2019/0269345 A1 | 9/2019 | Sriram | | |
| 2020/0008725 A1 | 1/2020 | Bach et al. | | |
| 2020/0107766 A1* | 4/2020 | Liu | ........................ | G16H 40/63 |
| 2020/0178888 A1* | 6/2020 | Nakae | ................ | G06K 9/00543 |
| 2021/0023332 A1* | 1/2021 | Auger | .................... | A61B 5/165 |
| 2021/0148675 A1* | 5/2021 | Stanley | ................ | G06V 40/174 |
| 2021/0259615 A1* | 8/2021 | Hendler | .................... | G06F 3/01 |
| 2021/0353224 A1* | 11/2021 | Etkin | ................... | A61B 5/4082 |
| 2021/0386343 A1* | 12/2021 | Goldenberg | ......... | A61B 5/1032 |
| 2021/0393182 A1* | 12/2021 | Chatterjee | ............. | G16H 40/67 |

OTHER PUBLICATIONS

Giulia Mele, et al., "Simultaneous EEG-fMRI for Functional Neurological Assessment", Frontiers in Neurology, vol. 10, Article 848, Aug. 13, 2019, pp. 1-11.

* cited by examiner

DEEP LEARNING MODEL-BASED IDENTIFICATION OF STRESS RESILIENCE USING ELECTROENCEPHALOGRAPH (EEG)

BACKGROUND

Technical Field

The present disclosure is directed to deep learning model-based identification of stress resilience using an electroencephalograph (EEG).

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Stress resilience is a characteristic that may reflect a person's vulnerability towards stressful events, and the capability of the person to adapt or maladapt, consciously and/or unconsciously, to the events. An objective measure of stress resilience using brain signals may provide an index of mental health. Researchers in the psychosocial fields have identified multi-dimensional characteristics of resilience. In studies that use associated factors to measure the stress resilience, the researchers may use several measuring instruments to ensure that multi-dimensional characteristic of resilience is addressed. Although, stress resilience is known to have valid psychometric properties, there is a limitation in the non-physiological approach, which only considers characteristics or levels of stress resilience and not the resiliency adaptation process. Hence, there is a need for a physiological-based stress intervention and stress resilience building programs that allow objective monitoring of human responses to stressful life events.

SUMMARY

In an exemplary embodiment, a method for identification of stress resilience, is disclosed. The method includes stimulating a human subject by at least one of a plurality of stressful events, acquiring multichannel real-time electroencephalograph (EEG) signals by an EEG monitor worn by a human subject, recording the real-time EEG signals received during the stressful event, transmitting the real-time EEG signals to a computing device, wherein the computing device has circuitry and program instructions including a deep learning model and a convolutional neural network, which when executed by one or more processors, cause the one or more processors to perform the steps of generating a plurality of filtered brain wave frequencies related to the stressful event by filtering the multichannel real-time EEG signals, classifying the brain wave frequencies by frequency level by applying the filtered brain wave frequencies to the deep learning model, applying each frequency level associated with the stressful event to the convolutional neural network, and identifying a level of stress resilience of the human subject associated with the stressful event.

In another exemplary embodiment, a system for identification of stress resilience is disclosed. The system includes an EEG monitor configured to acquire multichannel real-time electroencephalograph (EEG) signals from a brain of a human subject, a virtual reality headset, a plurality of bandpass filters configured to filter the multichannel real-time EEG signals by frequency range, a computing device connected to the EEG monitor, the virtual reality headset and the plurality of bandpass filters, the computing device having circuitry, including one or more processors, and program instructions including a deep learning model and a convolutional neural network, CNN, which when executed by the one or more processors, cause the one or more processors to present a plurality of stressful events to the human subject, receive the multichannel real-time EEG signals from the EEG monitor, generate a plurality of filtered brain wave frequencies related to the stressful event by filtering the real-time EEG signals by the plurality of bandpass filters, classify the brain wave frequencies by frequency level by applying the filtered brain wave frequencies to the deep learning model, apply each frequency level associated with the stressful event to the convolutional neural network and identify a level of stress resilience of the human subject associated with the stressful event.

In another exemplary embodiment, a non-transitory computer readable medium having instructions stored therein that, when executed by one or more processors, cause the one or more processors to perform a method of identifying stress resilience. The method includes stimulating a human subject by at least one of a plurality of stressful events, acquiring multichannel real-time electroencephalograph (EEG) signals by an EEG monitor worn by a human subject, recording the real-time EEG signals received during the stressful event, transmitting the real-time EEG signals to a computing device, wherein the computing device has circuitry and program instructions including a deep learning model and a convolutional neural network, which when executed by one or more processors, cause the one or more processors to perform the steps of generating a plurality of filtered brain wave frequencies related to the stressful event by filtering the multichannel real-time EEG signals, classifying the brain wave frequencies by frequency level by applying the filtered brain wave frequencies to the deep learning model, applying each frequency level associated with the stressful event to the convolutional neural network, and identifying a level of stress resilience of the human subject associated with the stressful event.

The foregoing general description of the illustrative embodiments and the following detailed description thereof are merely exemplary aspects of the teachings of this disclosure, and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

Figure 1:
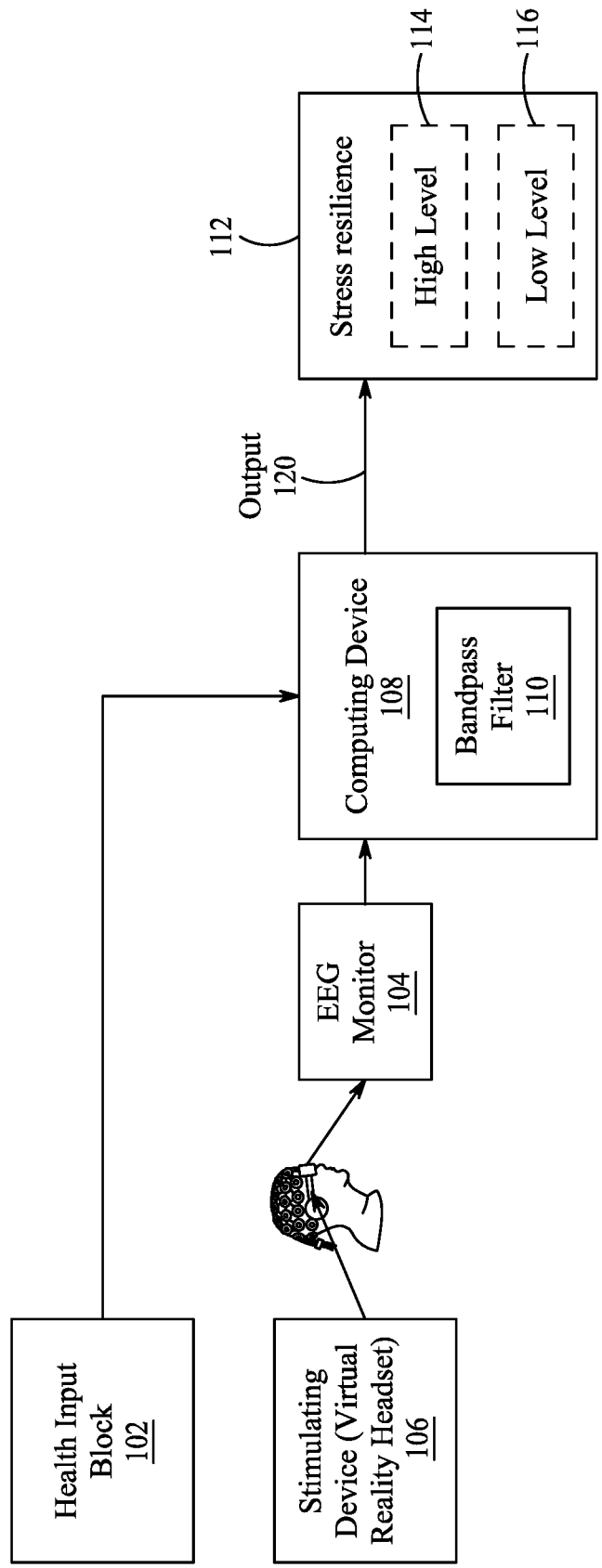
FIG. 1 illustrates a block diagram of a system for identifying stress resilience, according to certain embodiments.

In the drawings, like reference numerals designate identical or corresponding parts throughout the several views. Further, as used herein, the words "a," "an" and the like generally carry a meaning of "one or more," unless stated otherwise.

Furthermore, the terms "approximately," "approximate," "about," and similar terms generally refer to ranges that include the identified value within a margin of 20%, 10%, or preferably 5%, and any values therebetween.

Aspects of this disclosure are directed to a system, method and non-transitory computer readable medium method for identification of stress resilience. The disclosure provides a solution for identifying stress resilience using electroencephalogram (EEG) signals as a single modality approach. In some example implementations, virtual reality technology is used to induce stress conditions that emulate real-life stressful events to a human subject so that induced mental states from EEG can be used to identify stress resilience. Integrating the virtual reality technology to emulate a real-life environment supports identifying the stress resilience, as it may not be plausible to monitor brain responses in actual settings where the conditions and routines are complex and risky. The disclosure uses deep learning models with a convolutional neural network (CNN) to classify multichannel EEG signals into levels of stress resilience with a minimum of two levels (high/low) or more. The deep learning models are trained with EEG data from diverse, large population databases FIG. 1 illustrates a block diagram of a system for identifying stress resilience, according to one or more aspects of the present disclosure. FIG. 1 includes a health input block 102, an EEG monitor 104, a stimulating device 106 (also known as a virtual reality headset), and a computing device 108. The health input block 102 may be an input to the computing device 108. The health input block 102 may be a server, a data storage device, a database or an input device that provides digital information of a subject's health such as health records, consultation records, diagnosis records, and such records from a subject profile. In examples, some of the digital information may be of a human subject's physiological health and/or mental health. The EEG monitor 104 is a device that is used for performing EEG tests on the subject. In one or more aspects, the EEG test is used for determining electrical activity in a brain of the subject. The EEG test involves detachably applying electrodes to specific positions over the scalp of the subject. Each position is proximate to a different area of a brain of the human subject. Each of these specific positions is specified using, for example, the International 10/20 system. The International 10/20 system is an internationally recognized method to describe and apply the location of scalp electrodes for an EEG test. The system is based on the relationship between the location of an electrode and the underlying area of the brain, specifically the cerebral cortex. The 10 and 20 in the International 10/20 system may refer to placement of electrodes with distances between adjacent electrodes of about 10% or 20% of the total front-back or right-left distance of the skull. For example, a measurement is taken across the top of the head, from the nasion to the inion. An alternate method may include placing measurement electrodes starting at one ear and ending at the other ear, over the top of the head. Specific anatomical locations of the ear used may include the tragus, the auricle and the mastoid. Other standardized positions for placing the electrodes may be used. The electrodes may be made of stainless steel, tin, gold, or silver covered with a silver chloride coating. In some examples, the electrodes are attached using a conductive gel or paste after preparing the scalp area by light abrasion to reduce electrode-scalp impedance. Each electrode is labeled with a letter and a number. The letter may refer to an area of the brain underlying the electrode. For example, a letter F may refer to a frontal lobe, a letter T for a temporal lobe, a letter C for a central lobe, a letter P for a parietal lobe, and a letter O for an occipital lobe. Some electrodes that are placed at midline of the brain, are referred to as midline electrodes that are marked with a subscript z. Further, electrodes with even numbers may be applied onto a right side of the patent's head, and electrodes having odd numbers may be applied onto a left side of the subject's head. The electrodes may be passive electrodes, active electrodes, dry electrodes and sponge electrodes. The electrodes may be held in a mesh configuration to ensure their orientation does not change during the testing. The mesh may be cloth, rubber, a polymer or the like, which holds the electrodes in place. This may be referred to as an "electrode cap".

Figure 2:
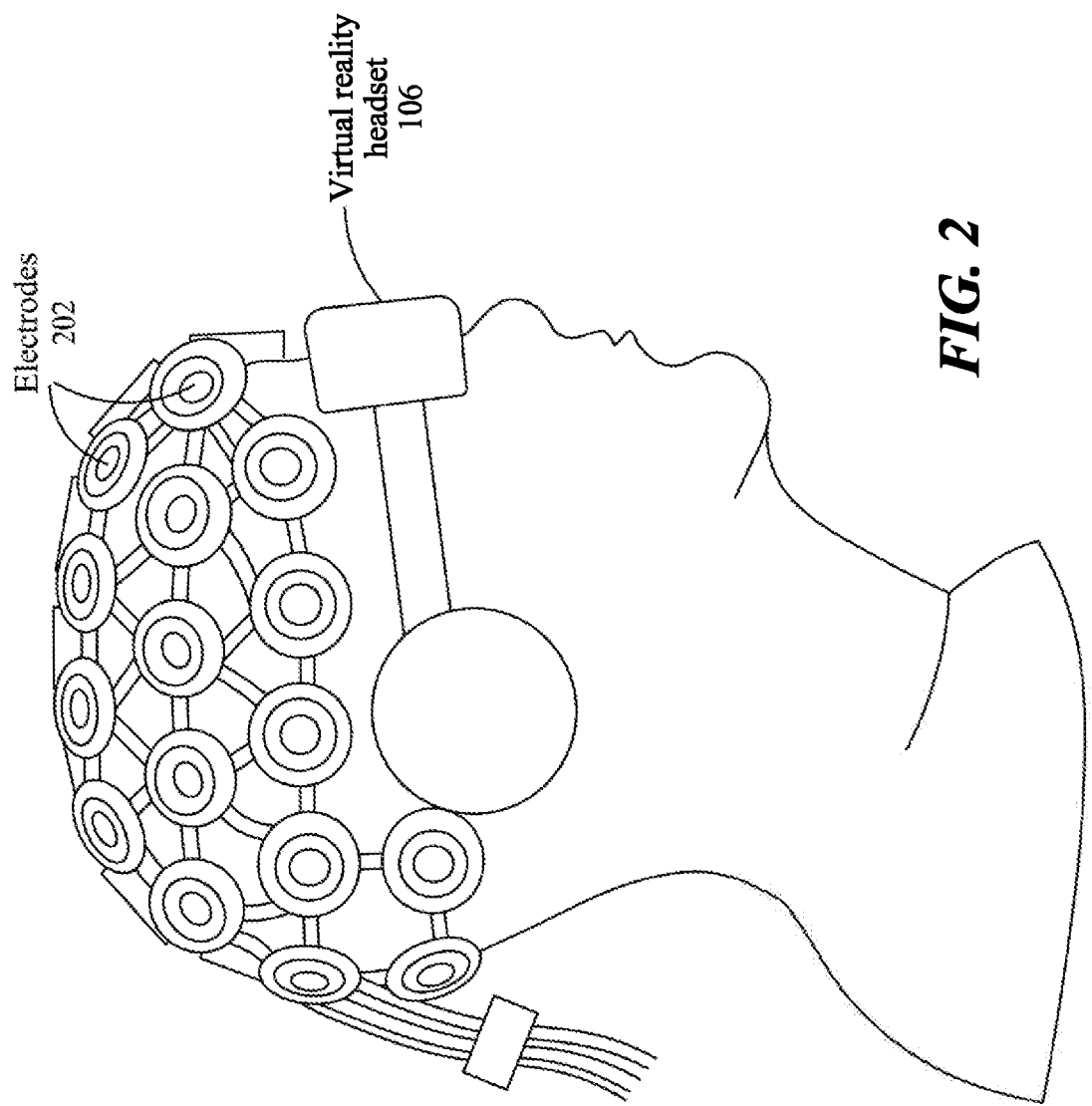
FIG. 2 is an exemplary illustration of placement of dense array of electrodes on a human scalp, according to certain embodiments.

Passive electrodes are individual electrodes made of silver/silver chloride (Ag—AgCl) which are attached to individual wires connected to EEG monitor 104. The passive electrodes may be individually attached to the subject's scalp. Active electrodes are strategically pre-placed in an electrode cap which is placed on the subject's scalp. The active electrodes do not require individual placement in comparison to the passive electrodes. Due to the pre-placement of electrodes in the electrode cap, time taken to perform EEG test is substantially reduced as the time taken to prepare the subject is minimal. The active electrodes are also made of silver/silver chloride (Ag—AgCl) suited for DC acquisition. The active electrode setup may include circuits and active shielding that support recordings at high transition resistances, minimize ambient noise, interference due to electrical effects, and artifacts due to cable movement. Similar to the active electrodes, the dry electrodes are electrodes strategically pre-placed in a cap-like structure, forming a setup that is placed on the subject's scalp. The dry electrodes set up is designed with flexible cap and mushroom-shaped supporting electrodes with adjustable length, which allows adapting the cap to any head geometry to establish optimum contact between the electrodes and the subject scalp to remove the necessity of conductive gel and for ease of application. Similar to the active electrodes and the dry electrodes, a sponge electrode setup is built in sponges designed thereof, with passive Ag/AgCl electrodes that are held in strategic places in a durable and flexible net or mesh. The sponge electrodes include sponge pockets to hold the passive Ag/AgCl electrodes or carbon rubber electrodes. The sponges are dampened and the electrode placed inside the sponge pocket. The dampened sponge electrodes in the mesh is placed on a subject head perform the EEG test. An example of using a dense array of electrodes in a sponge electrode setup to record the brain electrical activity of a subject is illustrated in FIG. 2. FIG. 2 illustrates a first plurality of electrodes 202 in a sponge electrode setup placed on a subject's head. These electrodes are coupled to a response pad which is further coupled to the EEG monitor 104.

The stimulating device 106 is configured to stimulate the subject by at least one of a plurality of stressful events. The stressful event may be any life event that may stimulate stress in the subject. The stressful events may be provided to the user through for example, virtual reality scripts presenting real-life scenarios, loud noises, images, and videos. The stimulating device 106 may include an audio unit, a video device, and/or a stimulating unit. The stimulation may include, but are not limited to, stimulation through audio, stimulation through video and/or through stimulation through a plurality of second electrodes (not shown). An example of the stimulating device 106 may be a display device such as a television that displays a recorded event. In another example, the stimulating device 106 may be a virtual reality device such as a virtual reality headset providing binaural audio and three dimensional graphics. In some example implementations, the stimulating device 106 may be a network of components that is designed for providing a three-dimensional stimulation or a virtual reality environment. In another example implementation, a home theatre setup may be used as a stimulating environment. The stimulation to the subject may be enhanced by placing each of a second plurality of electrodes on a different location on a body of the human subject not including the scalp. For example, the second plurality of electrodes may be placed on hands, legs, abdomen, legs, and such locations. During the stimulation, a low-level electrical stimulation may be transmitted through one or more of the second plurality of electrodes during one or more selected time periods of the stressful event. The use of the second plurality of electrodes enhances the stimulation effect on the subject. In a non-limiting example, a subject with army or law enforcement background may be stimulated with a stressful event by providing a counter-terrorist operation through a virtual reality scene. During the stimulation, effects of blast or shrapnel hits or bullet hits may be stimulated through these second plurality of electrodes by providing a low level electrical stimulation to areas of the body, which stimulation is harmless. In another example, a fire fighter may be stimulated with a stressful event by providing a fire extinguishing scenario. During the stimulation, effect of fire-related burns on the skin may stimulated through these second plurality of electrodes by providing a low-level electrical stimulation, although there would not be any injuries in reality. Aromas may be emitted by the virtual reality device to supplement the sensory experience. For example, an aroma of smoke may be provided during a firefighting scenario. In another non-limiting example, the subject may be stimulated with a stressful event of experiencing extortion. During the stimulation, an effect of knife stabbing may be stimulated through these second plurality of electrodes on the body by providing a low level electrical stimulation, although there would not be any injuries in reality.

The computing device 108 may be any device that may be used for identification of stress resilience. The computing device 108 may be a general purpose computer or a specially designed computer for identification of stress resilience. A bandpass filter 110 may be part of the computing device 108 or separate from the computing device 108 that is used for allowing signals between 0.5 Hz and 45 Hz.

In operation, the subject may be prepared for the EEG tests by placing the electrodes at appropriate locations on the scalp of the subject. The subject is stimulated by stress-free events using the stimulating device 106. The stress-free events may include any pleasant presentation of events such as life events or relaxing events such as providing media of natural landscapes such as sea waves, birds chirping, and such media. The stress-free events are provided after consultation with the subject on stress-free events that relaxes or calms the subject, ensuring that the general stress-free events are not stressful to the subject due to any life-related event associated with stress-free events. Response to the stress-free events may provide a baseline of the subject's response. The EEG monitor 104 acquires multichannel real-time EEG signals as a response to the stimulation by the subject through the plurality of first electrodes detachably attached to the human subject. The EEG monitor 104 captures electrical activity by recording electrical impulses in the subject's brain, and provides the real-time EEG signals as an output. The EEG monitor 104 may record the acquired the real-time EEG signals received during the stress-free event. The EEG monitor 104 may communicate the real-time EEG signals to the computing device 108. The computing device 108 may process the real-time EEG signals to determine whether the subject is experiencing any stress. The computing device 108 may use well-known or conventional techniques to process the real-time EEG signals to determine whether the subject is experiencing any stress. Upon identifying that the subject is stress-free, the computing device 108 identifies and records a baseline EEG frequency level related to the stress-free period of time.

The association of EEG brain waves at the resting state of the brain differs when the brain is responding to a stressful event. Having obtained the baseline EEG frequency level related to the stress-free period of time, in some aspects, the subject's stress resilience abilities may be determined. Stress resilience may be defined as a healthy adaptation process where an individual mobilizes resources from within to cope with adversity. To identify subject's stress resilience, the subject is stimulated by at least one of a plurality of stressful events using the stimulating device 106. In some examples, the stimulating device 106 may be a virtual reality device through which real-life scenarios are provided into a virtual environment. Some examples include scenarios where conditions involve risky or complex operations such as a workplace. In a non-limiting example, a rescue operation in a firefighting scene for a fireman may be a stressful scenario. In another example, an emergency lifesaving procedure on a critically injured subject may be a stressful scenario for healthcare personnel. In another non-limiting example, a stressful scenario may include a rape scene. The stimuli may trigger a stress resilience mechanism in the subject, which involves the subject attempting to cope with brain activity changes induced by the stress. During the stressful situation, the brain responds by paying selective attention to stimuli of the situation and appraising how demanding and relevant the situation is to their well-being and accesses resources the subject has to cope with the stressful situation. In some examples, physiological arousal is one of the responses to the stress and involves mobilization of resources to deal with stressful situations. During the stressful situations, it is observed that a level of emotional intensity is also fed back to cognitive appraisal, and therefore influences the appraisal component. In response to the cognitive appraisal and physiological arousal, the subject exhibits behavioral actions as a coping mechanism towards the stressful situation. The actions may orient the subject towards palliative emotion-regulating or direct problem-solving techniques.

The EEG monitor 104 acquires multichannel real-time EEG signals as a response to the stimulation by at least one of a plurality of stressful events from the subject, through the plurality of electrodes detachably located on the scalp of the human subject. The EEG monitor 104 may receive the real-time EEG signals from each different area of the brain. The EEG monitor 104 may record the acquired the real-time EEG signals received during the stressful event. The EEG monitor 104 may communicate the real-time EEG signals to the computing device 108. The computing device 108 includes circuitry and program instructions, including a deep learning model and a convolutional neural network (CNN). The computing device 108 may use a bandpass filter 110 (also 704, see FIG. 7) to obtain relevant EEG signals and eliminate unwanted signals below 0.5 Hz and above 45 Hz. The computing device 108 executes the program instructions to perform identification of stress resilience. As a part of performing identification of stress resilience, the computing device 108 may analyze a morphology of the EEG signals. Analyzing the morphology of the EEG signals includes determining shape of a waveform or an EEG pattern in the EEG signals based on frequencies that combine to make up the waveform and by phase and voltage relationships in the waveform. In some examples, EEG patterns in the EEG signals that are observed include monomorphic, polymorphic, sinusoidal, and transient. The monomorphic pattern demonstrates a distinct EEG activity appearing to be composed of one dominant activity. The polymorphic pattern demonstrates a distinct EEG activity composed of multiple frequencies that combine to form a complex waveform. The sinusoidal pattern may resemble sine waves which are mostly composed of monomorphic activity. The transient pattern demonstrates an isolated wave or pattern that is distinctly different from background activity. In some situations, there may be spikes or sharp waves, which are a part of transient wave patterns. The computing device 108 may filter the EEG signals to identify and eliminate artifacts that are due to the subject movements and/or electrical surges and the like in the EEG monitor 104. The subject-related artifact may be due to the physical movement of the subject, such as eye movements. The device-related artifacts may be due to cable movement, electrode movement due to improper attachment of an electrode and such factors. These artifacts are unwanted signals that distort the actual EEG signals.

The computing device 108 may process the EEG signals that are obtained after artifact elimination to filter and generate a plurality of filtered brain wave frequencies related to the stressful event by filtering the multichannel real-time EEG signals. The computing device 108 may use well known or proprietary techniques to filter the multichannel real-time EEG signals. The computing device 108 may classify the brain wave frequencies by frequency level by applying the filtered brain wave frequencies to a deep learning model(s). The deep learning model(s) is trained with EEG data from diverse, large population databases. Using the deep learning model(s), the computing device 108 may classify the brain wave frequencies into a delta frequency band, a theta frequency band, an alpha frequency band, a beta frequency band, a gamma frequency band, and such frequency bands. The delta frequency band may have a frequency range of 1 Hz to 4 Hz. The delta frequency band may have high amplitude values and slow waves. The delta frequency band may be seen frontally in adults and posteriorly in children. The delta frequency band may be observed when the subject is completely relaxed, particularly during deep sleep, meditation, or in a sedative state. The theta frequency band has a frequency of 3.5 to 7.5 Hz and is classified as slow activity. The theta frequency band may be observed when the subject has passive thoughts, in a drowsy condition, in a sleepy condition, and in a semi-attentive state. The alpha frequency band has a frequency between 7.5 and 13 Hz. The alpha frequency signals are usually seen in posterior regions of the head on each side. The alpha frequency signals have high amplitudes on the dominant side. The alpha frequency band is observed when the subject closes the eyes and relaxing, and fades when the subject opens the eyes or gets alerted. The alpha frequency band is associated with the subject being awake but in a resting state. The alpha frequency band is also found in adults who are in a calm and alert state. The alpha frequency band is a major frequency band seen in normal relaxed adults. The beta frequency band is found mostly during an active state of the subject. The beta frequency band has a frequency range of 12 Hz to 40 Hz. The beta frequency band is found on both sides of the head in symmetrical distribution and is most evidently found in the frontal portion of the head. The beta frequency band is generally observed when the subject is managing daily activities, that is, the subject may be awake, alert, busy, focused, and involved in daily and routine activities. The beta frequency band may be sub-classified into a low beta frequency band, a mid-beta frequency band, and a high-beta frequency band. The low beta frequency band frequency ranges from 12 Hz to 15 Hz, the mid-beta frequency band ranges from 15 Hz to 22 Hz, and the high-beta frequency band ranges from 22 Hz to 38 Hz. The low beta frequency band is observed when the subject is actively thinking. The mid-beta frequency band is observed when the subject is performing activities with focus. The high-beta frequency band is observed when the subject is anxious, excited, solving complex problems, and dealing with challenging situations. The gamma frequency band has a frequency range of 30 Hz to 80 Hz. The gamma frequency band is observed when the subject is thinking deeply and focused. The high frequency EEG signals (i.e., beta and gamma) may reflect a higher level of brain activity in response to stressful events. The computing device 108 identifies each frequency level associated with the stressful events. In some examples, for some subjects during the stressful events, the frequency level may be within the beta frequency band, and for some other subjects during the stressful events, the frequency level may be within the gamma frequency band. Some other subjects may exhibit a different frequency band during the stressful events. The computing device 108 may determine brain networks in each EEG frequency band (the delta frequency band, the theta frequency band, the alpha frequency band, the beta frequency band and the gamma frequency bands). For example, the computing device 108 may construct the brain networks using well known methods such as the EEG source-space connectivity method. The EEG source-space connectivity may include reconstructing dynamics of the cortical sources, and measuring functional connectivity between the reconstructed time series. Each of the frequency bands may be linked with specific functional roles. The computing device 108 determines links between the recorded EEG signals with the functional relationship between anatomical brain regions (e.g., networks), through the EEG inverse solution that provides a localization of the cortical sources originating these EEG signals. Further as described, the computing device filters the reconstructed time series into different frequency bands. The computing device 108 applies each frequency level associated with the stressful event to the CNN. The computing device 108 may process the EEG signals in the time domain within the aforementioned frequency level using unsupervised deep learning model(s) with CNN. The time-domain EEG signal from multichannel recording provides large data for the deep learning model to classify the level of stress resilience. The unsupervised deep learning model(s) with CNN may process the EEG signals in the time domain within the aforementioned frequency level to identify and obtain a level of stress resilience of the human subject associated with the stressful event. For example, the computing device 108 may classify and obtain a beta frequency band for a subject during a stressful event. The computing device 108 may apply the filtered beta frequency band associated with the stressful event to the unsupervised deep learning model with CNN. The unsupervised deep learning model with CNN processes the EEG signals in the filtered beta frequency band and generates a level of stress resilience of the human subject associated with the stressful event.

In some examples, the computing device 108 may define two levels: a low level of stress resilience and a high level of stress resilience. In some examples, the computing device 108 may define multiple levels of stress resilience. In some examples, the levels of stress resilience may be quantified using well known measuring scales such as Connor-Davidson Resilience Scale (CD-RISC), the Campbell-Sills and Stein scale or such scales. The Connor-Davidson Resilience Scale is a 25 divisional scale which is based on the Connor-Davidson operational definition of resilience, that is, an ability to thrive in the face of adversity. The Campbell-Sills and Stein scale is a boiled down version or 10 divisional scale based on the CD-RISC scale.

In some aspects, the computing device 108 may classify, by the deep learning model, the brain wave frequencies by the frequency band of a brain electrical activity, the area of the brain and a functional connectivity between different locations in the brain.

Measuring stress resilience includes a multi-process ranging from selective attention, cognitive appraisal, emotional arousal, and tendencies in behavioral actions. The computing device 108 may aggregate the EEG signals with the information from determinant factors and be used to identify markers for stress resilience.

The computing device 108 may access a database such as a health input block 102 configured with mental health conditions related to levels of stress resilience. The computing device 108 may match the level of stress resilience to a mental health condition. The computing device 108 may generate a report of the mental health condition.

Figure 3:
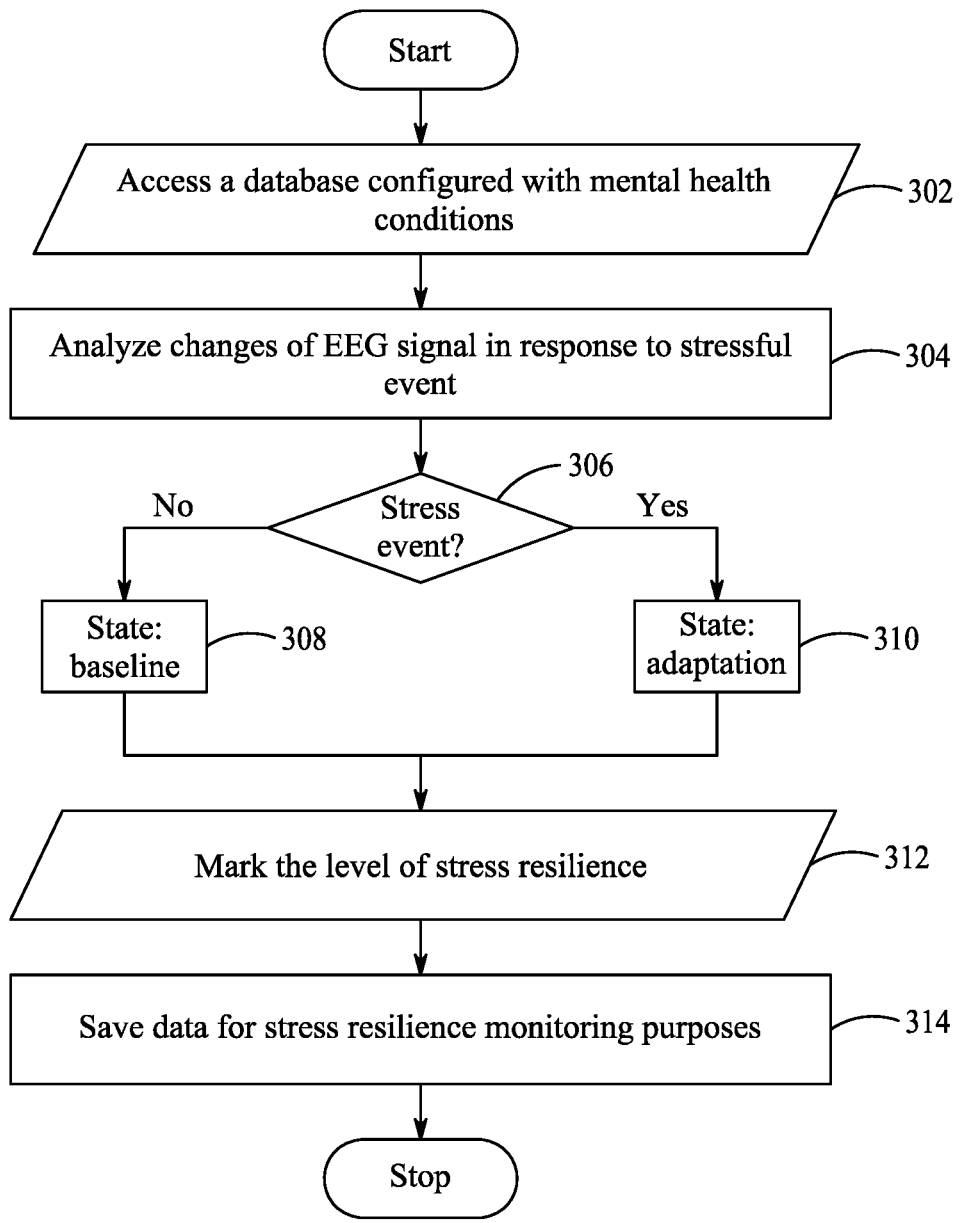
FIG. 3 illustrates a flow chart of data processed to output and monitor a stress resilience index, according to certain embodiments.

FIG. 1 illustrates an output 120 of the computing device 108 including identification of stress resilience 112. The stress resilience may be provided in two levels or multiple levels. The two levels may be a high level of stress resilience 114 and a low level of stress resilience 116. FIG. 3 illustrates a flow chart of data processed to output and monitor the stress resilience index, according to one or more aspects. In step 302, the computing device 108 may access a database configured with mental health conditions related to levels of stress resilience. Using the stimulating device 106, the subject is stimulated by at least one of a plurality of stressful events.

The EEG monitor 104 may receive and record the real-time EEG signals received from the subject as a result of the stimulation during the stressful event. In step 304, the computing device 108 may analyze the changes in the real-time EEG signal in response to the stressful event. In step 306, based on the changes in the real-time EEG signal, the computing device 108 may determine a level of stress resilience. If a level of stress resilience due to the stimulation is the same as a level of stress resilience during a stress-free event, then in step 308, the level of stress resilience is labeled as a baseline stress resilience of the person. Alternatively, if a level of stress resilience changes due to the stimulation of stressful events, then in step 310, the level of stress resilience is identified as an adaptation of stress resilience in response to the stressful event.

In step 312, the level of stress resilience is marked. In step 314, the computing device 108 may save the real-time EEG signal and level of stress resilience for stress resilience monitoring purposes. The computing device 108 may use or further monitor the saved EEG signal and the level of stress resilience information for monitoring longitudinally as more information is gathered from different life events. The term longitudinal refers to a process in which no particular trend overtime is expected, instead, an assessment is performed on how much responses vary over time for a given subject.

Figure 4:
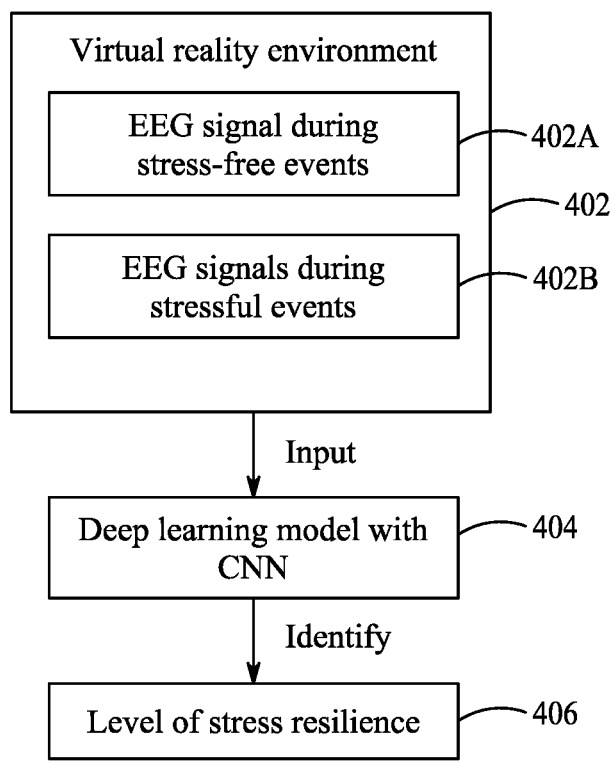
FIG. 4 illustrates a process flow to identify stress resilience using EEG signals recorded during stressful and resting conditions in a virtual environment, according to certain embodiments.

FIG. 4 illustrates a flow chart to identify stress resilience using EEG signals recorded during stressful and resting conditions in a virtual reality environment, according to one or more embodiments. The subject may be prepared by placing each electrode of the first plurality of electrodes on a location of a scalp of the human subject. Each location is proximate to a different area of a brain of the human subject. In step 402, the subject is stimulated using a virtual reality environment through the stimulating device 106. The stimulation is performed first with stress-free events and subsequently with stressful events, or vice versa. Step 402 may include two sub-steps 402A and 402B. Step 402A includes acquiring and recording the multichannel real-time EEG signals by the EEG monitor 104 through the first plurality of electrodes during stimulation of stress-free events or at rest. Step 402B includes acquiring and recording the multichannel real-time EEG signals by the EEG monitor 104 through the first plurality of electrodes during the stimulation of subject using stressful events. The multichannel real-time EEG signals recorded during the stress-free events and the stressful events are input to the computing device 108. The computing device 108 generates a plurality of filtered brain wave frequencies related to the stress-free and stressful events by filtering the multichannel real-time EEG signals. In step 404, the computing device 108 classifies the brain wave frequencies by frequency level by applying the filtered brain wave frequencies to the deep learning model. Further, the computing device 108 applies each frequency level associated with the stressful event to the CNN. In step 406, the computing device 108 identifies a level of stress resilience of the human subject associated with the stressful event.

Figure 5:
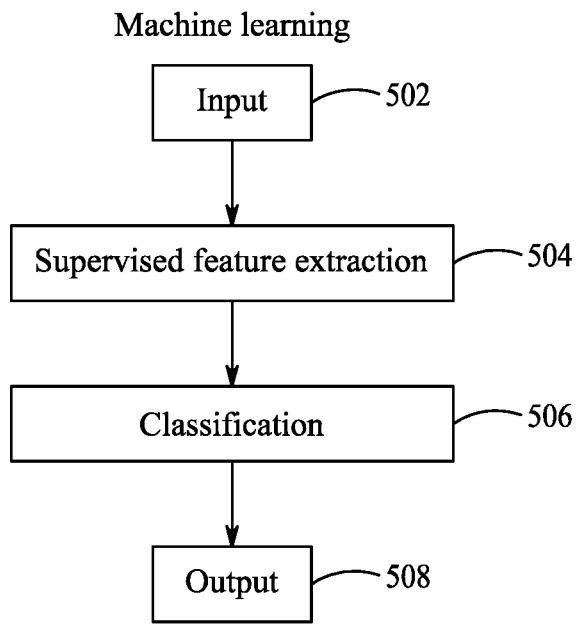
FIG. 5 illustrates a process flow for using machine learning models for identifying stress resilience, according to certain embodiments.

FIG. 5 illustrates a flow chart for using machine learning models for identifying stress resilience, according to one or more aspects of the present disclosure. In step 502, EEG data obtained from a large population test by stimulation during stress-free events and stressful events, may be provided as an input. In a non-limiting example, data from 5000 or greater subjects or volunteers may be obtained as the input for machine learning. In step 504, the computing device 108 may use one or more machine learning models to perform supervised feature extraction from the brain waves corresponding to the filtered multichannel real-time EEG signals. The supervised feature extraction generates a data output based on data points and/or previous machine learning deployments for feature extraction from the brain waves. For the supervised feature extraction from the brain waves, the computing device 108 may be provided with a collection of labeled data points called a training set that includes input brain waves and extracted features as output, using which the machine learning models learn to perform feature extraction from the brain waves. In step 506, the computing device 108 performs classification using one or more machine learning models to predict and assign a class label to extracted features from the brain wave frequencies that demonstrate stress resilience. In step 508, the computing device 108 provides updated one or more machine learning models for identifying stress resilience.

Figure 6:
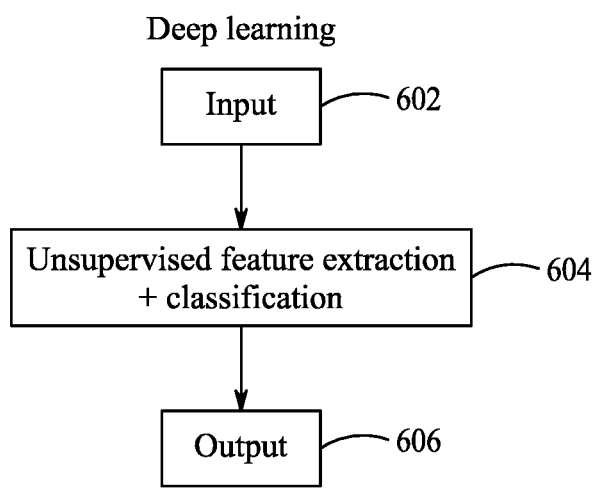
FIG. 6 illustrates a process flow for using the deep learning models for identifying stress resilience, according to certain embodiments.

FIG. 6 illustrates a flow chart for applying the measurements to a deep learning model configured to identify stress resilience, according to one or more embodiments. In step 602, EEG data obtained from a large population by performing stimulation using stress-free events and stressful events may be provided as an input to train the deep learning model. In a non-limiting example, data from 5000 or greater subjects or volunteers may be obtained as the input for deep learning. The greater the amount of historical data, the more accurate the identification of stress resilience by the deep learning models. In step 604, the computing device 108 may use one or more trained deep learning models to perform unsupervised feature extraction from the filtered multichannel real-time EEG signals in the time-domain within the frequency bands, and classification using the one or more machine learning models to assign a class label to extracted features from the EEG signals that demonstrate stress resilience. For the unsupervised feature extraction, the computing device 108 may be provided with the input, that is, the multichannel real-time EEG signals in the time-domain, and no corresponding output variables are provided, based on which the machine learning models learn to perform feature extraction. In step 606, the computing device 108 identifies a level of stress resilience based on output of the unsupervised feature extraction and classification. Using the deep learning models provides a robust approach to identify stress resilience without any need for specific neuro-markers that differentiate the level of stress resilience. The EEG signal input from multichannel recording provides a large quantity data for the deep learning model to classify the level of stress resilience of a particular subject.

Figure 7:
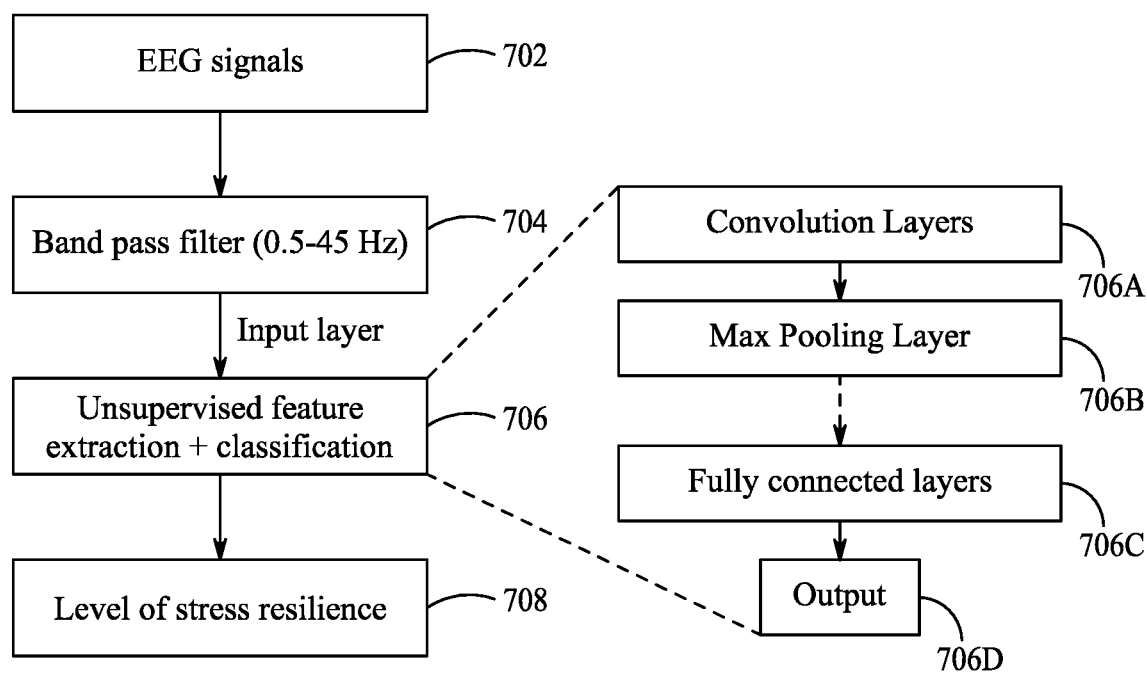
FIG. 7 illustrates a process flow for using the deep learning models with a convolutional neural network (CNN) to identify stress resilience, according to certain embodiments.

FIG. 7 illustrates a flow chart for using deep learning models with CNN to identify stress resilience, according to one or more embodiments. Incorporating the whole scalp area of the multichannel EEG signals received from stimulating the electrodes with over a plurality of frequency bands allows the deep learning model to learn the dynamic process of stress resilience ranging from selective attention, cognitive appraisal, emotional arousal, and tendencies in behavioral actions. In step 702, EEG signals obtained from a large population through stimulation using stress-free events and stressful events, may be provided as an input to train the model. In some examples, data from about 5000 or greater subjects or volunteers may be obtained as the input to train the deep learning model. In step 704, the EEG signals may be passed through bandpass filter 110 to filter signals beyond 0.5 Hz to 45 Hz range. In step 706, the computing device 108 may use one or more deep learning models to perform unsupervised feature extraction from the filtered multichannel real-time EEG signals, and classification using the one or more machine learning models to assign a class label to extracted features from the EEG signal that demonstrate stress resilience. In an aspect, the computing device 108 may use the CNN as part of step 706. The CNN comprises of a convolutional layer, a pooling layer, and fully connected layers, where each layer is given a filter size, strides, and padding parameters based on the input. The strides are a parameter that defines how the filter convolves around the input volume. In image processing, the strides may denote the number of pixels shifts over an input matrix in the convolution. In some examples, the stride may be predefined or the stride may be determined by the deep learning models based on historical processing. The padding parameter provides option to preserve original input volume which may be otherwise lost due to application of convolution. The padding parameter may be optionally used in CNN. In step 706A, a convolution layer that is first layer of the CNN may be applied. In some aspects, one or more convolution layers may be used. In a convolution layer, the computing device 108 may apply the EEG signals or brain waveforms images to one or more filters to extract different features. In some examples, multiple filters may be provided in the convolution layer. The convolution layer applies a convolution operation to the input, that is, the EEG signals to generate a result. In some aspects, padding may be used where feature maps produced by filter kernels in the convolution layers that are to be maintained the same size as original input. In step 706B, the pooling layer may be applied. In an example, there may be one or more pools. In one or more aspects, a max-pooling approach may be used in the pooling layer. The pooling layer progressively reduces a size of a EEG signal representation of the EEG signals to reduce a number of parameters and computation in a network. The pooling layer operates on each extracted feature independently. In step 706C, fully connected layers may be applied. The fully connected layers may be a feed-forward neural networks. The fully connected layers form the last few layers in the network. The fully connected layers in step 706C receive output of the convolution layers and the pooling layers as an input. The input may be flattened to be given as input to the fully connected layer. In an example, flattening the input may refer to converting the data into a 1-dimensional array for inputting to the fully connected layer. In step 706C, the fully connected layers forms the output classification of the CNN, in which the EEG signals are classified into levels of stress resilience. In step 706D, the levels are stress resilience are output. In step 708, the computing device 108 provides the levels are stress resilience. Using the deep learning models provides a robust approach to identify stress resilience without any need for specific neuro-markers that differentiate the level of stress resilience. The EEG signal input from multichannel recording provides large data for the deep learning model to classify the level of stress resilience.

Figure 8:
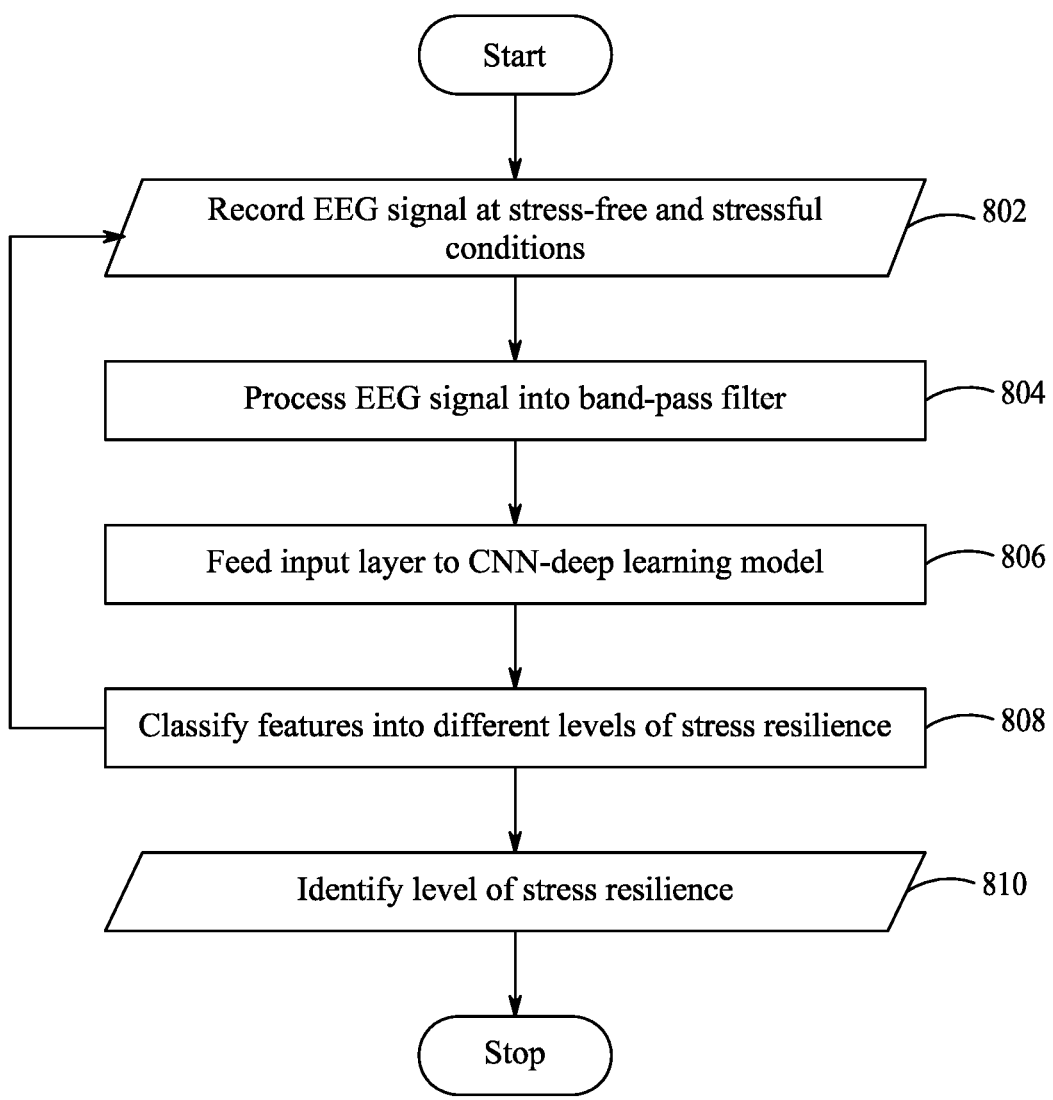
FIG. 8 illustrates a flow chart for identifying stress resilience using EEG signals using the deep learning models with the CNN, according to certain embodiments

FIG. 8 illustrates a process flow for using deep learning with CNN to identify stress resilience, according to one or more embodiments. In step 802, EEG signals may be recorded from the subject in a stress-free (resting state) and stressful state. In step 804, the EEG signals may be passed through the bandpass filter 110 that allows 0.5 Hz to 45 Hz frequencies to pass. In step 806, the output of the bandpass filter 110 may be fed into the computing device 108 using deep learning models with CNN. The computing device 108 may use the one or more deep learning models with CNN to classify features from the brain wave frequencies into different levels of stress resilience. In some aspects, the classified features may be fed back to step 804 as the input. In step 810, the computing device 108 identifies the level of stress resilience. As more EEG signals are recorded, the deep learning model will be continuously trained to identify the stress resilience of the subject.

Identification of stress resilience may be used as a physiological measure to assess the risk of an individual in developing mental illness. The stress resilience identification method, as described in the present disclosure, can be used in cognitive-behavioral therapy in both clinical and non-clinical populations. The use of the stress resilience identification methods and system of the present disclosure to objectively monitor stress resilience during the presence of stressful events with the integration of virtual reality minimizes the complexity of data collection setup in assessing mental health.

The stress resilience can be identified at a minimum of two levels (high/low) or more as the deep learning model is trained with EEG data from diverse, large population databases.

The EEG method of identifying stress resilience is non-invasive and economical. Unlike fMRI-based research that investigate the brain activity, the EEG method does not require a dedicated space and does not require subjects to be immobile. The fMRI devices limits the movement of a person as they are required to be in supine position throughout the procedure and therefore this device cannot be used in collecting data involving any task performance. Also, the fMRI devices are expensive devices requiring expert and trained technicians to set up and operate. The procedure of collection fMRI data is noisy, and are highly susceptible to physiological noise due to motion. Further a minimum initial setup cost for the fMRI modality is at least 10 times the cost required for a maximum initial setup cost for EEG modality. In contrast, the EEG method and device is simple to use, user-friendly, particularly for claustrophobic subjects who cannot use the fMRI. Also, the EEG devices do not require a dedicated space. The EEG device is portable and provides a high temporal resolution.

The first embodiment is illustrated with respect to FIGS. 1-11. The first embodiment describes a method for identification of stress resiliencies described. The method includes stimulating a human subject by at least one of a plurality of stressful events, acquiring multichannel real-time EEG signals by the EEG monitor 104 worn by a human subject, recording the real-time EEG signals received during the stressful event, transmitting the real-time EEG signals to the computing device 108, wherein the computing device 108 has circuitry and program instructions including a deep learning model and a convolutional neural network, which when executed by one or more processors, cause the one or more processors to perform the steps of generating a plurality of filtered brain wave frequencies related to the stressful event by filtering the multichannel real-time EEG signals, classifying the brain wave frequencies by frequency level by applying the filtered brain wave frequencies to the deep learning model, applying each frequency level associated with the stressful event to the convolutional neural network, and identifying a level of stress resilience of the human subject associated with the stressful event.

The method further includes acquiring real-time EEG signals during a stress-free period of time, and identifying a baseline EEG frequency level related to the stress-free period of time.

The method further includes stimulating the human subject with the stressful event in a virtual reality environment.

The method further includes acquiring multichannel real-time EEG signals by an EEG monitor 104 having a first plurality of electrodes, by placing each electrode of the first plurality of electrodes on a location of a scalp of the human subject, each location proximate to a different area of a brain of the human subject, receiving real-time EEG signals from each different area of the brain, and filtering the plurality of brain wave frequencies into delta, theta, alpha, beta, and gamma frequency bands.

The method further includes classifying, by the deep learn model, the brain wave frequencies by the frequency band of a brain electrical activity, the area of the brain and a functional connectivity between different locations in the brain.

The method further includes identifying a level of stress resilience, by the convolutional neural network, by matching each frequency band of the filtered brain wave frequencies to one of a delta, a theta, an alpha, a beta, and a gamma frequency band, wherein each frequency band is related to a brain activity response to the stressful event.

The method further includes accessing, by the computing device 108, a database configured with mental health conditions related to levels of stress resilience, matching the level of stress resilience to a mental health condition, and generating a report of the mental health condition.

The virtual reality environment includes binaural audio and three dimensional graphics presented by a virtual reality headset.

The method further includes placing each of a second plurality of electrodes on a different location on a body of the human subject not including the scalp, and transmitting a low level electrical stimulation through each of the second plurality of electrodes during one or more selected time periods of the stressful event.

The method further includes stimulating the human subject by at least one of a plurality of stressful events including one or more of virtual reality scripts presenting real-life scenarios, loud noises, images, and videos.

The second embodiment is illustrated with respect to FIGS. 1-11. The second embodiment describes a system for identification of stress resilience. The system includes the EEG monitor 104 configured to acquire multichannel real-time EEG signals from a brain of a human subject, a virtual reality headset, a plurality of bandpass filters configured to filter the multichannel real-time EEG signals by frequency range, a computing device 108 connected to the EEG monitor 104, the virtual reality headset and the plurality of bandpass filters, the computing device 108 having circuitry, including one or more processors, and program instructions including a deep learning model and a convolutional neural network, CNN, which when executed by the one or more processors, cause the one or more processors to: present a plurality of stressful events to the human subject, receive the multichannel real-time EEG signals from the EEG monitor, generate a plurality of filtered brain wave frequencies related to the stressful event by filtering the real-time EEG signals by the plurality of bandpass filters, classify the brain wave frequencies by frequency level by applying the filtered brain wave frequencies to the deep learning model, apply each frequency level associated with the stressful event to the convolutional neural network, and identify a level of stress resilience of the human subject associated with the stressful event.

The virtual reality headset is configured with binaural audio and three dimensional graphics.

The system of further includes a memory operatively connected with the computing device 108. The memory is configured to store a plurality of virtual reality scripts presenting real-life stressful situations. The computing device 108 is configured to transmit at least one of the plurality of virtual reality scripts to the virtual reality headset. The virtual reality headset is configured to present the at least one virtual reality script to the human subject. The EEG monitor 104 is configured to acquire the multichannel real-time EEG signals from each area of the brain stimulated by the at least one virtual reality script.

The deep learning model is configured to classify the brain wave frequencies by a frequency band of brain electrical activity, the area of the brain and a functional connectivity between different locations in the brain.

The plurality of bandpass filters are configured to filter the multichannel real-time EEG signals into a plurality of frequency bands consisting of delta, theta, alpha, beta, and gamma frequency bands.

The system further includes a database operatively connected to the computing device 108, wherein the database is configured with mental health conditions related to levels of stress resilience. The computing device 108 is further configured to match the level of stress resilience to a mental health condition, and generate a report of the mental health condition.

The third embodiment is illustrated with respect to FIGS. 1-11. The third embodiment describes a non-transitory computer readable medium having program instructions stored therein that, when executed by one or more processors, cause the one or more processors to perform a method for identification of stress resilience. The method includes stimulating a human subject by at least one of a plurality of stressful events, acquiring multichannel real-time electroencephalograph (EEG) signals by an EEG monitor 104 worn by a human subject, recording the real-time EEG signals received during the stressful event, transmitting the real-time EEG signals to a computing device 108, wherein the computing device 108 has circuitry and program instructions including a deep learning model and a convolutional neural network, which when executed by one or more processors, cause the one or more processors to perform the steps of generating a plurality of filtered brain wave frequencies related to the stressful event by filtering the multichannel real-time EEG signals, classifying the brain wave frequencies by frequency level by applying the filtered brain wave frequencies to the deep learning model, applying each frequency level associated with the stressful event to the convolutional neural network, and identifying a level of stress resilience of the human subject associated with the stressful event.

Figure 9:
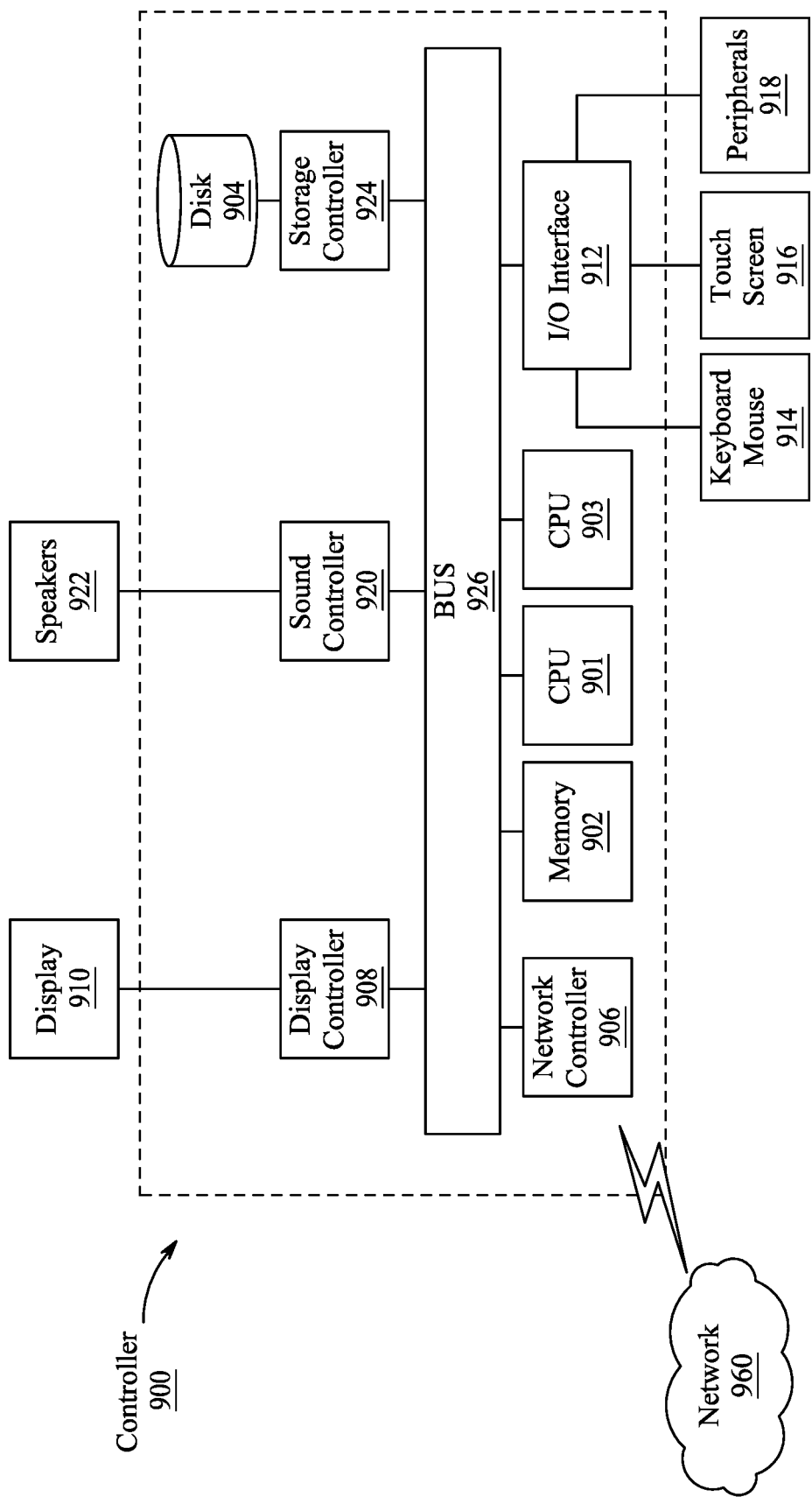
FIG. 9 is an illustration of a non-limiting example of details of computing hardware used in the computing system, according to certain embodiments.

The non-transitory computer readable medium method further includes classifying, by the deep learn model, the brain wave frequencies by the frequency band of a brain electrical activity, the area of the brain and a functional connectivity between different locations in the brain, identifying a level of stress resilience, by the convolutional neural network, by matching each frequency band of the filtered brain wave frequencies to one of a delta, a theta, an alpha, a beta, and a gamma frequency band, wherein each frequency band is related to a brain activity response to the stressful event, accessing, by the computing device 108, a database configured with mental health conditions related to levels of stress resilience, matching the level of stress resilience to a mental health condition, generating a report of the mental health condition. Next, further details of the hardware description of the computing environment of FIG. 1 according to exemplary embodiments is described with reference to FIG. 9. In FIG. 9, a controller 900 is described is representative of the computing device 108 of FIG. 1 in which the controller is a computing device which includes a CPU 701 which performs the processes described above/below. The process data and instructions may be stored in memory 902. These processes and instructions may also be stored on a storage medium disk 904 such as a hard drive (HDD) or portable storage medium or may be stored remotely.

Further, the claims are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the computing device communicates, such as a server or computer.

Further, the claims may be provided as a utility application, background daemon, or component of an operating system, or combination thereof, executing in conjunction with CPU 901, 903 and an operating system such as Microsoft Windows 9, Microsoft Windows 10, UNIX, Solaris, LINUX, Apple MAC-OS and other systems known to those skilled in the art.

The hardware elements in order to achieve the computing device may be realized by various circuitry elements, known to those skilled in the art. For example, CPU 901 or CPU 903 may be a Xenon or Core processor from Intel of America or an Opteron processor from AMD of America, or may be other processor types that would be recognized by one of ordinary skill in the art. Alternatively, the CPU 901, 903 may be implemented on an FPGA, ASIC, PLD or using discrete logic circuits, as one of ordinary skill in the art would recognize. Further, CPU 901, 903 may be implemented as multiple processors cooperatively working in parallel to perform the instructions of the inventive processes described above.

The computing device in FIG. 9 also includes a network controller 906, such as an Intel Ethernet PRO network interface card from Intel Corporation of America, for interfacing with network 960. As can be appreciated, the network 960 can be a public network, such as the Internet, or a private network such as an LAN or WAN network, or any combination thereof and can also include PSTN or ISDN sub-networks. The network 960 can also be wired, such as an Ethernet network, or can be wireless such as a cellular network including EDGE, 3G and 4G wireless cellular systems. The wireless network can also be WiFi, Bluetooth, or any other wireless form of communication that is known.

The computing device further includes a display controller 908, such as a NVIDIA GeForce GTX or Quadro graphics adaptor from NVIDIA Corporation of America for interfacing with display 910, such as a Hewlett Packard HPL2445w LCD monitor. A general purpose I/O interface 912 interfaces with a keyboard and/or mouse 914 as well as a touch screen panel 916 on or separate from display 910. General purpose I/O interface also connects to a variety of peripherals 918 including printers and scanners, such as an OfficeJet or DeskJet from Hewlett Packard.

A sound controller 920 is also provided in the computing device such as Sound Blaster X-Fi Titanium from Creative, to interface with speakers/microphone 922 thereby providing sounds and/or music.

The general purpose storage controller 924 connects the storage medium disk 904 with communication bus 926, which may be an ISA, EISA, VESA, PCI, or similar, for interconnecting all of the components of the computing device. A description of the general features and functionality of the display 910, keyboard and/or mouse 914, as well as the display controller 908, storage controller 924, network controller 906, sound controller 920, and general purpose I/O interface 912 is omitted herein for brevity as these features are known.

The exemplary circuit elements described in the context of the present disclosure may be replaced with other elements and structured differently than the examples provided herein. Moreover, circuitry configured to perform features described herein may be implemented in multiple circuit units (e.g., chips), or the features may be combined in circuitry on a single chipset, as shown on FIG. 10.

Figure 10:
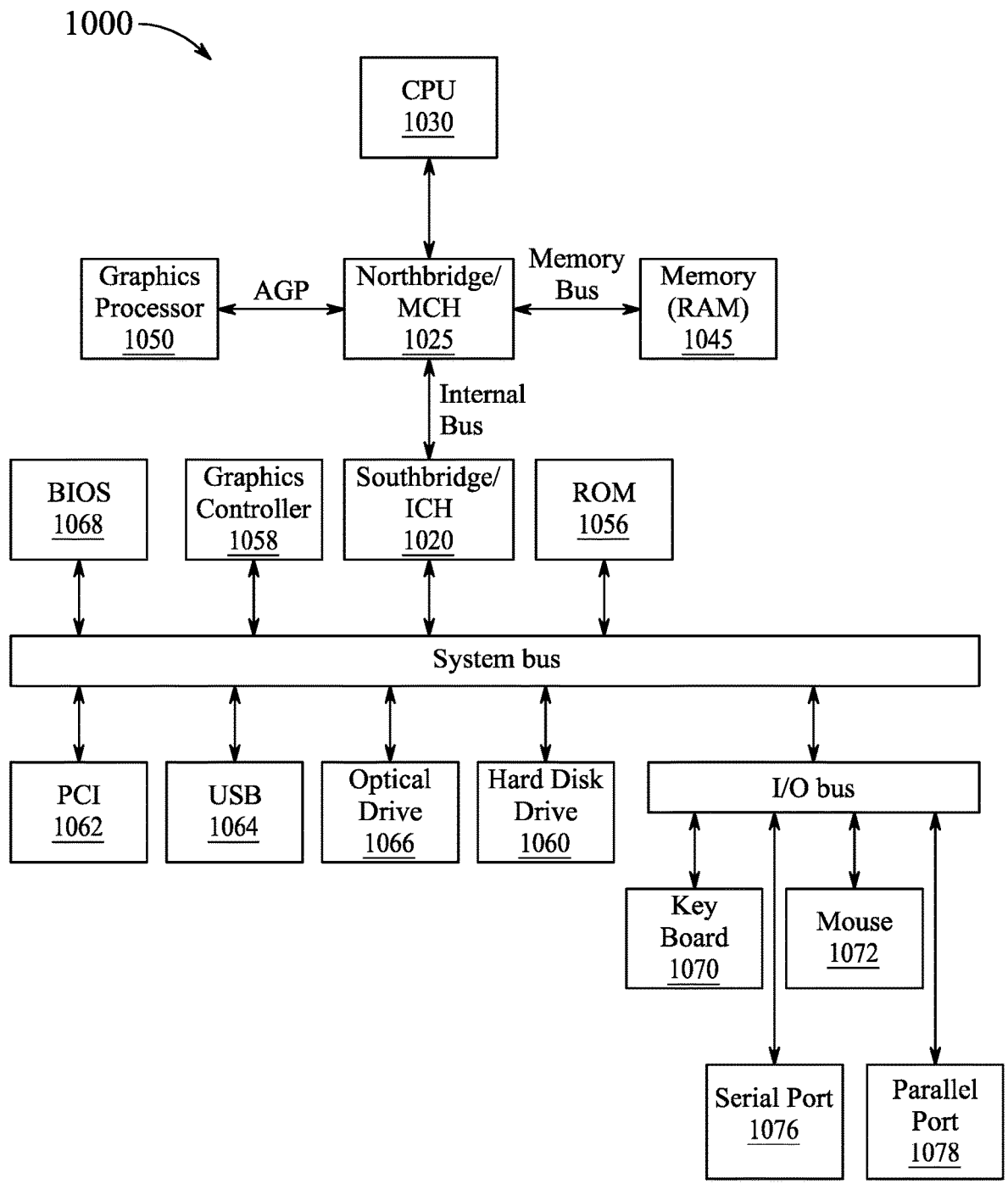
FIG. 10 is an exemplary schematic diagram of a data processing system used within the computing system, according to certain embodiments.

FIG. 10 shows a schematic diagram of a data processing system 1000 used within the computing system, according to exemplary aspects of the present disclosure. The data processing system 1000 is an example of a computer in which code or instructions implementing the processes of the illustrative aspects of the present disclosure may be located.

In FIG. 10, data processing system 1000 employs a hub architecture including a north bridge and memory controller hub (NB/MCH) 1025 and a south bridge and input/output (I/O) controller hub (SB/ICH) 1020. The central processing unit (CPU) 1030 is connected to NB/MCH 1025. The NB/MCH 1025 also connects to the memory 1045 via a memory bus, and connects to the graphics processor 1050 via an accelerated graphics port (AGP). The NB/MCH 1025 also connects to the SB/ICH 1020 via an internal bus (e.g., a unified media interface or a direct media interface). The CPU Processing unit 1030 may contain one or more processors and even may be implemented using one or more heterogeneous processor systems.

Figure 11:
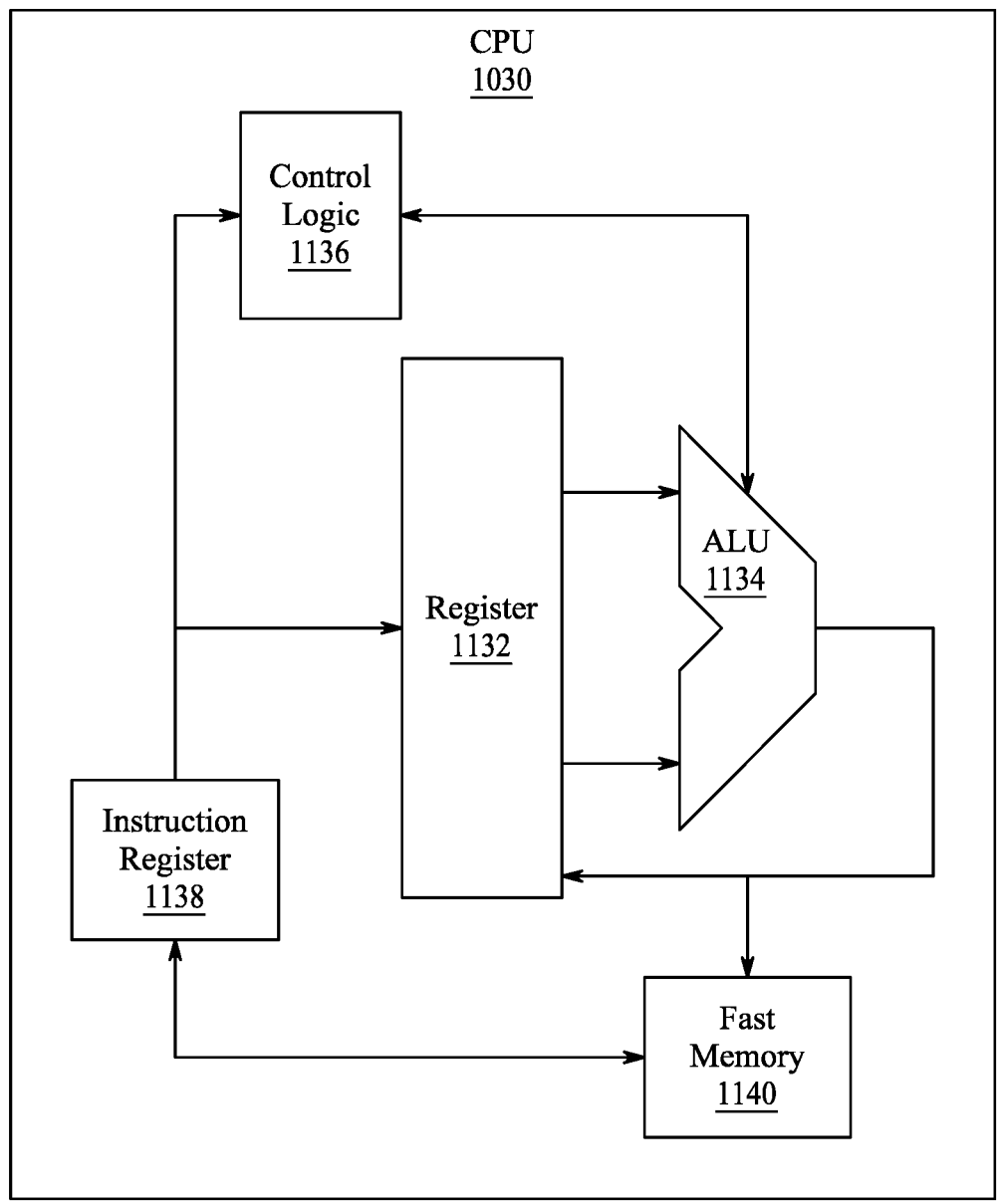
FIG. 11 is an exemplary schematic diagram of a processor used with the computing system, according to certain embodiments.

For example, FIG. 11 shows one aspects of the present disclosure of CPU 1030. In one aspects of the present disclosure, the instruction register 1138 retrieves instructions from the fast memory 1140. At least part of these instructions is fetched from the instruction register 1138 by the control logic 1136 and interpreted according to the instruction set architecture of the CPU 1030. Part of the instructions can also be directed to the register 1132. In one aspects of the present disclosure the instructions are decoded according to a hardwired method, and in other aspects of the present disclosure the instructions are decoded according to a microprogram that translates instructions into sets of CPU configuration signals that are applied sequentially over multiple clock pulses. After fetching and decoding the instructions, the instructions are executed using the arithmetic logic unit (ALU) 1134 that loads values from the register 1132 and performs logical and mathematical operations on the loaded values according to the instructions. The results from these operations can be feedback into the register and/or stored in the fast memory 1140. According to certain aspects of the present disclosures, the instruction set architecture of the CPU 1030 can use a reduced instruction set architecture, a complex instruction set architecture, a vector processor architecture, a very large instruction word architecture. Furthermore, the CPU 1030 can be based on the Von Neuman model or the Harvard model. The CPU 1030 can be a digital signal processor, an FPGA, an ASIC, a PLA, a PLD, or a CPLD. Further, the CPU 1030 can be an x86 processor by Intel or by AMD; an ARM processor, a Power architecture processor by, e.g., IBM; a SPARC architecture processor by Sun Microsystems or by Oracle; or other known CPU architecture.

Referring again to FIG. 10, the data processing system 1000 can include that the SB/ICH 1020 is coupled through a system bus to an I/O Bus, a read only memory (ROM) 1056, universal serial bus (USB) port 1064, a flash binary input/output system (BIOS) 1068, and a graphics controller 1058. PCI/PCIe devices can also be coupled to SB/ICH 1020 through a PCI bus 1062.

The PCI devices may include, for example, Ethernet adapters, add-in cards, and PC cards for notebook computers. The Hard disk drive 1060 and CD-ROM 1056 can use, for example, an integrated drive electronics (IDE) or serial advanced technology attachment (SATA) interface. In one aspects of the present disclosure the I/O bus can include a super I/O (SIO) device.

Further, the hard disk drive (HDD) 1060 and optical drive 1066 can also be coupled to the SB/ICH 1020 through a system bus. In one aspects of the present disclosure, a keyboard 1070, a mouse 1072, a parallel port 1078, and a serial port 1076 can be connected to the system bus through the I/O bus. Other peripherals and devices that can be connected to the SB/ICH 1020 using a mass storage controller such as SATA or PATA, an Ethernet port, an ISA bus, an LPC bridge, SMBus, a DMA controller, and an Audio Codec.

Moreover, the present disclosure is not limited to the specific circuit elements described herein, nor is the present disclosure limited to the specific sizing and classification of these elements. For example, the skilled artisan will appreciate that the circuitry described herein may be adapted based on changes on battery sizing and chemistry, or based on the requirements of the intended back-up load to be powered.

Figure 12:
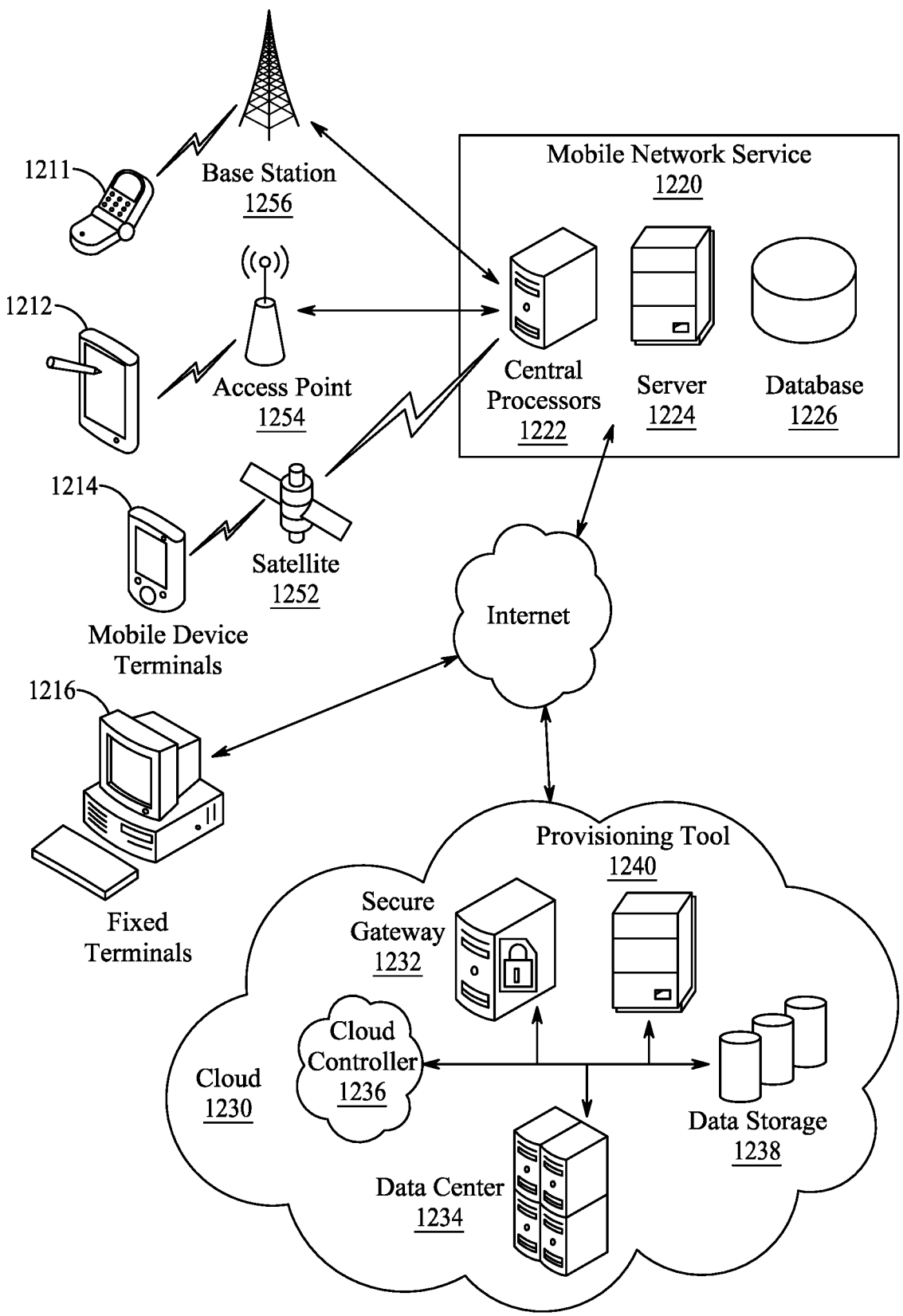
FIG. 12 is an illustration of a non-limiting example of distributed components which may share processing with the controller, according to certain embodiments.

The functions and features described herein may also be executed by various distributed components of a system. For example, one or more processors may execute these system functions, wherein the processors are distributed across multiple components communicating in a network. The distributed components may include one or more client and server machines, which may share processing, as shown by FIG. 12, in addition to various human interface and communication devices (e.g., display monitors, smart phones, tablets, personal digital assistants (PDAs)). The network may be a private network, such as a LAN or WAN, or may be a public network, such as the Internet. Input to the system may be received via direct user input and received remotely either in real-time or as a batch process. Additionally, some aspects of the present disclosures may be performed on modules or hardware not identical to those described. Accordingly, other aspects of the present disclosures are within the scope that may be claimed.

The above-described hardware description is a non-limiting example of corresponding structure for performing the functionality described herein.

Obviously, numerous modifications and variations of the present disclosure are possible in light of the above teachings. It is therefore to be understood that within the scope of the appended claims, the invention may be practiced otherwise than as specifically described herein.

The invention claimed is:

1. A method for identification of stress resilience, comprising:

stimulating a human subject by at least one of a plurality of stressful events;

acquiring multichannel real-time electroencephalograph (EEG) signals by an EEG monitor worn by a human subject;

recording the real-time EEG signals received during the stressful event;

transmitting the real-time EEG signals to a computing device, wherein the computing device has circuitry and program instructions including a deep learning model and a convolutional neural network, which when executed by one or more processors, cause the one or more processors to perform the steps of:

generating a plurality of filtered brain wave frequencies related to the stressful event by filtering the multichannel real-time EEG signals;

classifying the brain wave frequencies by frequency level by applying the filtered brain wave frequencies to the deep learning model;

applying each frequency level associated with the stressful event to the convolutional neural network; and identifying a level of stress resilience of the human subject associated with the stressful event.

2. The method of claim 1, further comprising:
acquiring real-time EEG signals during a stress-free period of time; and
identifying a baseline EEG frequency level related to the stress-free period of time.

3. The method of claim 1, further comprising:
stimulating the human subject with the stressful event in a virtual reality environment.

4. The method of claim 1, further comprising:
acquiring multichannel real-time EEG signals by an EEG monitor having a first plurality of electrodes, by:
placing each electrode of the first plurality of electrodes on a location of a scalp of the human subject, each location proximate to a different area of a brain of the human subject;
receiving real-time EEG signals from each different area of the brain; and
filtering the plurality of brain wave frequencies into delta, theta, alpha, beta, and gamma frequency bands.

5. The method of claim 4, further comprising:
classifying, by the deep learning model, the brain wave frequencies by the frequency band of a brain electrical activity, the area of the brain and a functional connectivity between different locations in the brain.

6. The method of claim 5, further comprising:
identifying a level of stress resilience, by the convolutional neural network, by matching each frequency band of the filtered brain wave frequencies to one of a delta, a theta, an alpha, a beta, and a gamma frequency band, wherein each frequency band is related to a brain activity response to the stressful event.

7. The method of claim 6, further comprising:
accessing, by the computing device, a database configured with mental health conditions related to levels of stress resilience;
matching the level of stress resilience to a mental health condition; and
generating a report of the mental health condition.

8. The method of claim 7, further comprising:
identifying, by the convolutional neural network, each area of the brain stimulated by the stressful event;
identifying, by the convolutional neural network, each of the areas of the brain in which the frequency band of the multichannel EEG signals are the same band; and
including, by the computing device, the areas of the brain which are the same band as the functional connectivity of the areas of the brain in the report of the mental health condition.

9. The method of claim 8, wherein the virtual reality environment includes binaural audio and three dimensional graphics presented by a virtual reality headset.

10. The method of claim 4, further comprising:
placing each of a second plurality of electrodes on a different location on a body of the human subject not including the scalp; and
transmitting a low level electrical stimulation through each of the second plurality of electrodes during one or more selected time periods of the stressful event.

11. The method of claim 1, further comprising stimulating the human subject by at least one of a plurality of stressful events including one or more of:
virtual reality scripts presenting real-life scenarios;
loud noises;
images; and
videos.

12. A system for identification of stress resilience, comprising:
an EEG monitor configured to acquire multichannel real-time electroencephalograph (EEG) signals from a brain of a human subject;
a virtual reality headset;
a plurality of bandpass filters configured to filter the multichannel real-time EEG signals by frequency range;
a computing device connected to the EEG monitor, the virtual reality headset and the plurality of bandpass filters, the computing device having circuitry, including one or more processors, and program instructions including a deep learning model and a convolutional neural network, CNN, which when executed by the one or more processors, cause the one or more processors to:
present a plurality of stressful events to the human subject;
receive the multichannel real-time EEG signals from the EEG monitor;
generate a plurality of filtered brain wave frequencies related to the stressful event by filtering the real-time EEG signals by the plurality of bandpass filters;
classify the brain wave frequencies by frequency level by applying the filtered brain wave frequencies to the deep learning model;
apply each frequency level associated with the stressful event to the convolutional neural network; and
identify a level of stress resilience of the human subject associated with the stressful event.

13. The system of claim 12, wherein the virtual reality headset is configured with binaural audio and three dimensional graphics.

14. The system of claim 13, further comprising:
a memory operatively connected with the computing device, wherein the memory is configured to store a plurality of virtual reality scripts presenting real-life stressful situations;
wherein the computing device is configured to transmit at least one of the plurality of virtual reality scripts to the virtual reality headset;

wherein the virtual reality headset is configured to present the at least one virtual reality script to the human subject; and wherein the EEG monitory is configured to acquire the multichannel real-time EEG signals from each area of the brain stimulated by the at least one virtual reality script.

15. The system of claim 12, wherein the deep learning model is configured to classify the brain wave frequencies by a frequency band of brain electrical activity, the area of the brain and a functional connectivity between different locations in the brain.

16. The system of claim 15, wherein the plurality of bandpass filters are configured to filter the multichannel real-time EEG signals into a plurality of frequency bands consisting of delta, theta, alpha, beta, and gamma frequency bands.

17. The system of claim 16, further comprising:
a database operatively connected to the computing device, wherein the database is configured with mental health conditions related to levels of stress resilience;
wherein the computing device is further configured to:
match the level of stress resilience to a mental health condition; and
generate a report of the mental health condition.

18. The system of claim 16, further comprising one or more of:
a plurality of virtual reality scripts configured to present real-life scenarios of at least one of a stressful and a non-stressful event;
a speaker configured to present loud noises;
a display configured to present stressful images; and
a plurality of videos configured to present video clips of at least one of a stressful and a non-stressful event.

19. A non-transitory computer readable medium having program instructions stored therein that, when executed by one or more processors, cause the one or more processors to perform a method for identification of stress resilience, comprising:
stimulating a human subject by at least one of a plurality of stressful events;
acquiring multichannel real-time electroencephalograph (EEG) signals by an EEG monitor worn by a human subject;
recording the real-time EEG signals received during the stressful event;
transmitting the real-time EEG signals to a computing device, wherein the computing device has circuitry and program instructions including a deep learning model and a convolutional neural network, which when executed by one or more processors, cause the one or more processors to perform the steps of:
generating a plurality of filtered brain wave frequencies related to the stressful event by filtering the multichannel real-time EEG signals;
classifying the brain wave frequencies by frequency level by applying the filtered brain wave frequencies to the deep learning model;
applying each frequency level associated with the stressful event to the convolutional neural network; and
identifying a level of stress resilience of the human subject associated with the stressful event.

20. The non-transitory computer readable medium method of claim 19, further comprising:
classifying, by the deep learning model, the brain wave frequencies by the frequency band of a brain electrical activity, the area of the brain and a functional connectivity between different locations in the brain;
identifying a level of stress resilience, by the convolutional neural network, by matching each frequency band of the filtered brain wave frequencies to one of a delta, a theta, an alpha, a beta, and a gamma frequency band, wherein each frequency band is related to a brain activity response to the stressful event;
accessing, by the computing device, a database configured with mental health conditions related to levels of stress resilience;
matching the level of stress resilience to a mental health condition;
generating a report of the mental health condition;
including, by the computing device, the areas of the brain which are the same band as the functional connectivity of the areas of the brain in the report of the mental health condition.

* * * * *